(12) United States Patent
Shi et al.

(10) Patent No.: US 11,793,764 B2
(45) Date of Patent: Oct. 24, 2023

(54) SIRNA NANOCAPSULE AND PREPARATION METHOD AND USE THEREOF

(71) Applicant: HENAN UNIVERSITY, Kaifeng (CN)

(72) Inventors: Bingyang Shi, Kaifeng (CN); Yan Zou, Kaifeng (CN)

(73) Assignee: HENAN UNIVERSITY, Kaifeng (CN)

( * ) Notice: Subject to any disclaimer, the term of this patent is extended or adjusted under 35 U.S.C. 154(b) by 236 days.

(21) Appl. No.: 17/112,547

(22) Filed: Dec. 4, 2020

(65) Prior Publication Data

US 2021/0322330 A1    Oct. 21, 2021

(30) Foreign Application Priority Data

Apr. 21, 2020 (CN) .......................... 202010319659.9

(51) Int. Cl.
*A61K 9/51* (2006.01)
*C12N 15/113* (2010.01)

(52) U.S. Cl.
CPC .......... *A61K 9/5138* (2013.01); *A61K 9/5192* (2013.01); *C12N 15/113* (2013.01); *C12N 2310/14* (2013.01)

(58) Field of Classification Search
CPC .. A61K 9/5138; A61K 9/5192; A61K 9/0019; A61K 9/5146; A61K 31/713; A61K 47/64; A61K 47/6933; C12N 15/113; C12N 2310/14; C12N 15/111; C12N 2320/32; B82Y 5/00; A61P 35/00
See application file for complete search history.

(56) References Cited

U.S. PATENT DOCUMENTS

| 2015/0071999 A1* | 3/2015 | Lu ........................ A61K 9/5192 424/463 |
| 2017/0173169 A1* | 6/2017 | Yantasee ............ A61K 47/6849 |

FOREIGN PATENT DOCUMENTS

WO     2012/079043    *    6/2012

OTHER PUBLICATIONS

English Translation of Office Action received for CN2020103196599 dated Mar. 15, 2021.
English Abstracts of cited Non-English patent documents for CN109880021A, CN109453114A, CN109893660A, CN108355139A, CN103566379A, CN106890336A, CN104530256A, CN106137968A, CN107095859A, CN103193979A, and CN106729749A.

* cited by examiner

*Primary Examiner* — Gollamudi S Kishore
(74) *Attorney, Agent, or Firm* — Billion & Armitage

(57) ABSTRACT

The present disclosure provides an siRNA nanocapsule and a preparation method and use thereof, relating to the technical field of biomedical engineering. The siRNA nanocapsule provided in the present disclosure includes siRNA and a shell encapsulating the siRNA and polymerized by a monomer A and a monomer B. The monomer A has a double bond at one end, and is electrostatically bound with the siRNA, and the monomer B includes molecules for improving tumor microenvironment sensitivity. The siRNA nanocapsule provided in the present disclosure is suitable for a wide range of clinical applications.

4 Claims, 5 Drawing Sheets

SIRNA NANOCAPSULE AND PREPARATION METHOD AND USE THEREOF

CROSS-REFERENCE TO RELATED APPLICATION

The present disclosure claims priority of Chinese patent application with the filing number 2020103196599 filed on Apr. 21, 2020 with the Chinese Patent Office, and entitled "siRNA Nanocapsule and Preparation Method and Use thereof", the contents of which are incorporated herein by reference in entirety.

TECHNICAL FIELD

The present disclosure relates to the technical field of biomedical engineering, in particular to an siRNA nanocapsule and a preparation method and use thereof.

BACKGROUND ART

Glioblastoma (GBM) is an invasive human intracranial malignant tumor with high mortality and high incidence, and still cannot be cured up to now. The clinical treatment means for GBM patients is to surgically remove the tumor to the maximum degree, followed by chemotherapy. Although combined treatment is carried out in a variety of ways, the median value of overall survival time of the patients is not prolonged to more than 15 months. More and more evidences prove that complexity of GBM and individual differences of patients are causes of ineffectiveness of current treatment methods.

RNA interference (RNAi) with high specificity and low toxicity is believed as an extremely promising method for treating various intractable GBMs. A double-stranded small interfering RNA (siRNA), one of effector molecules of RNA interference, theoretically can inhibit expression of any target gene, and has been listed as the most potential therapeutic agent for gene type diseases. However, naked siRNA enters serum and is easily degraded by nuclease, moreover, siRNA is negatively charged and has strong hydrophilicity, so that it cannot easily penetrate the cell membrane to enter the cytoplasm to exert an efficient RNAi effect. Thus, the key to siRNA application is to find a safe and effective delivery carrier. Viruses show outstanding siRNA delivery capability, but mutagenic toxicity and immunogenicity severely hinder their clinical application. Comparatively, non-viral carriers, such as cationic liposomes, polymers and inorganic nanoparticles, can deliver siRNA, but they still face problems of delivery efficiency and safety. Most non-viral delivery nano-carriers are cationic or liposome materials, and they have an excess amount of surface positive charges, usually cause systemic toxicity, and have relatively low selectivity in vivo. Besides, the blood brain barrier and low drug release efficiency also limit the therapeutic effect of the drug.

In view of this, the present disclosure is specifically proposed.

SUMMARY

The present disclosure provides an siRNA nanocapsule, including siRNA and a shell encapsulating the siRNA, wherein the siRNA is linked to the shell by electrostatic bonding; and the shell is obtained mainly by polymerizing a monomer A and a monomer B, and a targeting ligand is further linked outside the shell, wherein the monomer A can be electrostatically bound with the siRNA, and includes molecules with a double bond at one end; and the monomer B includes molecules for improving tumor microenvironment sensitivity.

The present disclosure further provides use of the above siRNA nanocapsule in preparation of a medicament for treating tumor; and preferably, the tumor is glioblastoma, non-small cell lung cancer or cervical cancer.

Besides, the present disclosure further provides a method for preparing the above siRNA nanocapsule, including making a monomer A electrostatically bound with siRNA and a monomer B to undergo polymerization reaction to obtain a shell, and then linking a targeting ligand to the shell to obtain the siRNA nanocapsule, wherein the monomer A includes molecules with a double bond at one end; and the monomer B includes molecules for improving tumor microenvironment sensitivity and molecules for linking the targeting ligand.

BRIEF DESCRIPTION OF DRAWINGS

In order to more clearly illustrate specific embodiments of the present disclosure or technical solutions in the prior art, accompanying drawings which need to be used in the description of the specific embodiments or the prior art will be introduced briefly below. Apparently, the accompanying drawings in the following description are for some embodiments of the present disclosure, while a person ordinarily skilled in the art still could obtain other drawings in light of these accompanying drawings, without using creative efforts.

DETAILED DESCRIPTION OF EMBODIMENTS

Figure 1:
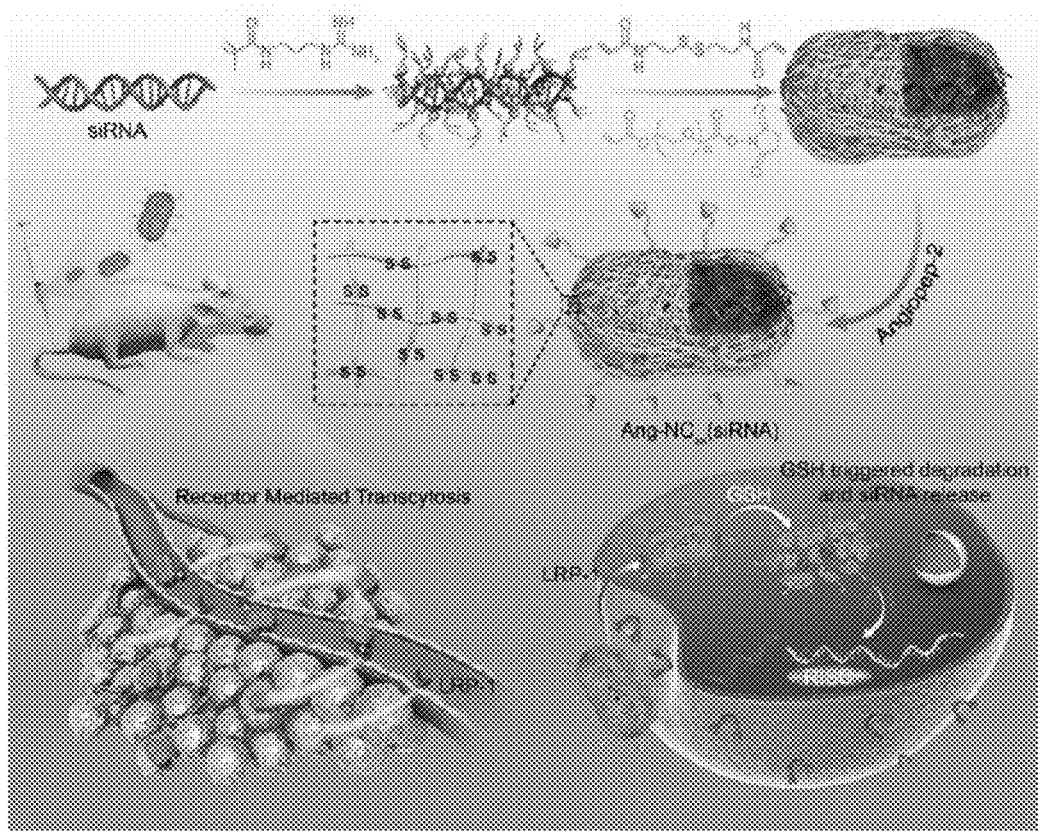
FIG. 1 is an illustration of preparation of an siRNA nanocapsule provided in the present disclosure, effective blood brain barrier penetration, highly specific GBM targeting, responsive drug release and gene silencing.

Unless otherwise defined herein, scientific and technical terms used in the present disclosure should have meanings that are commonly understood by those ordinarily skilled in the art. The meanings and scopes of the terms should be clear, however, in the case of any potential ambiguity, the definitions provided herein take precedence over any dictionary or foreign definitions. In the present disclosure, use of "or" means "and/or" unless otherwise stated. In addition, use of the term "include (comprise)" and other forms is non-limiting.

Generally, nomenclature for cell and tissue culture, molecular biology, immunology, microbiology, genetics and protein and nucleic acid chemistry and hybridization described herein and technologies thereof are those well-known and commonly used in the art. Unless otherwise stated, the methods and technologies in the present disclosure are generally carried out according to conventional methods well-known in the art and as described in various general and more specific references, and the references are cited and discussed throughout the present specification. Enzymatic reactions and purification technologies are carried out according to the manufacturer's instructions, as commonly realized in the art, or as described herein. Nomenclature used for analytical chemistry, synthetic organic chemistry and medical and pharmaceutical chemistry described herein, as well as laboratory procedures and technologies, are those well-known and commonly used in the art.

A first object of the present disclosure is to provide an siRNA nanocapsule, so as to at least relieve one of the technical problems existing in the prior art.

A second object of the present disclosure is to provide use of the above siRNA nanocapsule in preparation of a medicament for treating tumors.

A third object of the present disclosure is to provide a method for preparing the above siRNA nanocapsule.

The present disclosure provides an siRNA nanocapsule, including siRNA and a shell encapsulating the siRNA, wherein the siRNA is linked to the shell by electrostatic bonding; and the shell is obtained mainly by polymerizing a monomer A and a monomer B, and a targeting ligand is further linked outside the shell, wherein the monomer A can be electrostatically bound with the siRNA, and includes molecules with a double bond at one end; and the monomer B includes molecules for improving tumor microenvironment sensitivity.

Further, the monomer A includes guanidyl acrylate, spermine acrylate or N-(3-aminopropyl)methacrylamide; preferably, the molecules for improving tumor microenvironment sensitivity include molecules for improving reduction sensitivity, molecules for improving acid sensitivity or molecules for improving ROS response, and the molecules for improving reduction sensitivity are preferred; preferably, the molecules for improving reduction sensitivity include molecules containing a disulfide bond, and more preferably include biscystamine acrylamide; preferably, the monomer B further includes molecules for linking a targeting ligand; preferably, the molecules for linking the targeting ligand have one end linked to the molecules for improving tumor microenvironment sensitivity, and the other end linked to the targeting ligand, preferably including acrylate polyethylene glycol succinyl carboxymethyl ester, acrylate polyethylene glycol maleimide or acrylate hyaluronic acid succinyl methyl ester; and preferably, the targeting ligand includes Angiopep-2, RGD peptide, apolipoprotein E or transferrin, preferably Angiopep-2.

The present disclosure further provides use of the above siRNA nanocapsule in preparation of a medicament for treating tumor; and preferably, the tumor is glioblastoma, non-small cell lung cancer or cervical cancer.

Besides, the present disclosure further provides a method for preparing the above siRNA nanocapsule, including making a monomer A electrostatically bound with siRNA and a monomer B to undergo polymerization reaction to obtain a shell, and then linking a targeting ligand to the shell to obtain the siRNA nanocapsule, wherein the monomer A includes molecules with a double bond at one end; and the monomer B includes molecules for improving tumor microenvironment sensitivity and molecules for linking the targeting ligand.

Further, after mixing the siRNA with the monomer A, the monomer B is added, and radicals on the surface of siRNA undergo polymerization reaction under the action of an initiator and an optional catalyst, to form the shell encapsulating the siRNA; preferably, the monomer A includes guanidyl acrylate, spermine acrylate or N-(3-aminopropyl) methacrylamide; preferably, the molecules for improving tumor microenvironment sensitivity include molecules for improving reduction sensitivity, molecules for improving acid sensitivity or molecules for improving ROS response, and the molecules for improving reduction sensitivity are preferred; preferably, the molecules for improving reduction sensitivity include molecules containing a disulfide bond, and more preferably include biscystamine acrylamide; preferably, the monomer B further includes molecules for linking a targeting ligand; preferably, the molecules for linking the targeting ligand have one end linked to the molecules for improving tumor microenvironment sensitivity, and the other end linked to the targeting ligand, preferably including acrylate polyethylene glycol succinyl carboxymethyl ester, acrylate polyethylene glycol maleimide or acrylate hyaluronic acid succinyl methyl ester; preferably, the targeting ligand includes Angiopep-2, RGD peptide, apolipoprotein E or transferrin, preferably Angiopep-2; preferably, the initiator includes ammonium persulfate, preferably 0.05%-0.2% w/v ammonium persulfate solution, more preferably 0.1% w/v ammonium persulfate solution; and preferably, the catalyst includes N,N,N',N'-tetramethylethylenediamine, preferably 0.2%-0.8% w/v N,N,N',N'-tetramethylethylenediamine solution, more preferably 0.5% w/v N,N,N',N'-tetramethylethylenediamine solution.

Further, after mixing siRNA with guanidyl acrylate, biscystamine acrylamide and acrylate polyethylene glycol succinyl carboxymethyl ester are added, and the radicals on the surface of siRNA undergo polymerization reaction under the action of ammonium persulfate and N,N,N',N'-tetramethylethylenediamine, to form the shell encapsulating the siRNA; preferably, a molar ratio of siRNA to guanidyl acrylate after mixing is 1:200-250, preferably 1:220; and preferably, a molar ratio among guanidyl acrylate, biscystamine acrylamide and acrylate polyethylene glycol succinyl carboxymethyl ester is 3-8:3-8:1, preferably 5:5:1.

Further, the siRNA is mixed with the guanidyl acrylate by means of stirring; preferably, the stirring includes at least one of the following conditions: the time is 10-20 minutes, and the temperature is 20-25° C.; and preferably, the stirring is carried out at the temperature of 20-25° C. for 15 minutes.

Further, the polymerization reaction includes at least one of the following conditions: the polymerization reaction is carried out in an oxygen-free environment, the temperature is 0-5° C., and the time is 25-35 minutes; and preferably, the polymerization reaction is carried out in an oxygen-free environment at a temperature of 0° C. for 30 minutes.

Further, after the shell is formed, the targeting ligand is added to carry out a linking reaction to obtain the siRNA nanocapsule; preferably, the targeting ligand includes Angiopep-2; preferably, a molar ratio of the Angiopep-2 to acrylate polyethylene glycol succinyl carboxymethyl ester is 2-5:1, preferably 3:1; preferably, the linking reaction includes at least one of the following conditions: the temperature is 20-25° C., and the time is 1.8-2.2 hours; and preferably, the linking reaction is carried out at a temperature of 20-25° C. for 2 hours.

Further, 10 μL of guanidyl acrylate is added to 500 μL of siRNA aqueous solution, and the resultant is stirred at 20-25° C. for 15 minutes to obtain a mixed liquid of siRNA and guanidyl acrylate in a molar ratio of 1:220; to the mixed liquid 20 μL of biscystamine acrylamide and 90 μL of acrylate polyethylene glycol succinyl carboxymethyl ester are added, to render a molar ratio among guanidyl acrylate, biscystamine acrylamide and acrylate polyethylene glycol succinyl carboxymethyl ester to be 5:5:1, then 20 μL of 0.1% ammonium persulfate solution and 10 μL of 0.5% N,N,N', N'-tetramethylethylenediamine solution are added. After polymerization reaction is carried out in an oxygen-free environment at 0° C. for 30 minutes, 45 μg of Angiopep-2 is added and linking reaction is carried out at 20-25° C. for 2 hours, to obtain the siRNA nanocapsule, wherein a molar ratio of the Angiopep-2 to acrylate polyethylene glycol succinyl carboxymethyl ester is 3:1; preferably, after the linking reaction, a step of removing impurities is further included, and then the siRNA nanocapsule is obtained; and preferably, the impurities are removed with a molecular weight cut-off of 10 kDa.

Compared with the prior art, the present disclosure has the following beneficial effects:

(1) the siRNA nanocapsule provided in the present disclosure includes the siRNA and the shell encapsulating the siRNA obtained by polymerizing the monomer A and the monomer B. In the above, the monomer A can be electrostatically bound to the siRNA, and on one hand, the shell encapsulating the siRNA can be naturally formed after the monomer B and the monomer A are polymerized, thereby achieving nearly 100% of the siRNA encapsulation, and maximally protecting the siRNA against degradation; on the other hand, the concentration of siRNA is further facilitated, small-sized siRNA nanocapsule is realized, and cell membrane penetration rate is improved. In the above, the monomer A has a double bond at one end, and can be effectively linked to other monomers, thereby improving the stability of the nanocapsule.

(2) By introducing the molecules for improving tumor microenvironment sensitivity, the tumor microenvironment sensitivity of the siRNA nanocapsule provided in the present disclosure can be enhanced, thus a convenient condition is provided for triggered release of the siRNA nanocapsule at a lesion site, and the release efficiency of the siRNA is improved.

(3) In the present disclosure, the targeting ligand is linked to the surface of the siRNA nanocapsule, thus endowing the siRNA nanocapsule provided in the present disclosure with the targeting capability, so that it has higher delivery efficiency.

(4) Compared with existing delivery carriers, the siRNA nanocapsule provided in the present disclosure has both good biocompatibility and biosafety, and has the potential to be widely used in clinics.

According to one aspect of the present disclosure, an siRNA nanocapsule is provided, including siRNA and a shell encapsulating the siRNA, wherein the siRNA is linked to the shell by electrostatic binding; the shell is manly obtained by polymerizing a monomer A and a monomer B, and a targeting ligand is further linked outside the shell; the monomer A can be electrostatically bound with the siRNA, and includes molecules with a double bond at one end; and the monomer B includes molecules for improving tumor microenvironment sensitivity.

siRNA

Small interfering RNA (siRNA), being capable of specifically and directly regulating the target gene expression and meanwhile having extremely low cytotoxicity, is therefore considered as an effective means for treating various types of malignant tumors. When used to treat GBM, the siRNA may be selected from PLK1, Bcl-2, VEGFR2 or PDL1, etc.

Targeting Ligand

The targeting ligand can mediate endocytosis through receptor overexpressed by tumor cells, be selectively concentrated and positioned at molecular structures of target tissues, target organs, and target cells. Linking the targeting ligand outside the shell of the siRNA nanocapsule provided in the present disclosure can endow the siRNA nanocapsule with active targeting capability, so that it has higher delivery efficiency, and it is more helpful to increase the aggregation amount of the desired siRNA at the target site, and meanwhile, the siRNA nanocapsule is prevented from being swallowed by healthy tissues and causing injury, thus improving biosafety. Optionally, the targeting ligand includes Angiopep-2, RGD peptide, apolipoprotein E or transferrin.

The existence of blood brain barrier (BBB) makes it difficult for the drug to reach the glioma site in human brain, so that it becomes one of the most intractable tumors in cancer treatment. As a self-balancing defensive mechanism of brain, on one hand, BBB ensures the central nervous system to be protected from foreign substances, maintains an efficient steady state, and meanwhile inputs nutrients into the brain; on the other hand, the dense structure of BBB also hinders the therapeutic drug from entering the brain through non-invasive administration. As BBB endothelial cell and GBM tissue both highly express receptor-related protein 1 (LRP-1), when the siRNA nanocapsule provided in the present disclosure is applied for treating GBM, the targeting ligand is preferably Angiopep-2. The specific LRP-1 ligand Angiopep-2 is coupled on the surface of the siRNA nanocapsule provided in the present disclosure, and the Angiopep-2 (ANG) modified siRNA nanocapsule can specifically bind to low-density lipoprotein (LRP) receptor overexpressed on brain endothelial cells and brain glioma cells, and can also significantly enhance BBB permeability of the siRNA nanocapsule while targeting the brain glioma cells.

Monomer A

In the present disclosure, the shell of the siRNA nanocapsule is obtained by polymerizing the monomer A and the monomer B, the monomer A is electrostatically bound with the siRNA. On one hand, the shell encapsulating the siRNA can be naturally formed after the monomer B and the monomer A are polymerized, thereby achieving nearly 100% of the siRNA encapsulation, and maximally protecting the siRNA against degradation; on the other hand, the concentration of siRNA is further facilitated, small-sized siRNA nanocapsule is realized, and cell membrane penetration rate is improved. Particularly, the monomer A has a double bond at one end, and can be linked to other monomers, thereby improving the stability of the nanocapsule.

In some preferred embodiments, the monomer A includes guanidyl acrylate, spermine acrylate or N-(3-aminopropyl) methacrylamide. All of the above monomers A are positively charged, facilitating endocytosis of cells.

It should be noted that the guanidyl acrylate is self-made by the inventors in laboratory, and has a molecular structure as shown in formula I:

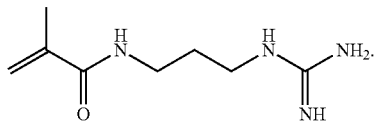

Formula I

Monomer B

Conventional nanomedicine carriers generally release the anticancer drug slowly by diffusion or hydrolysis of polymers, thus improving the drug resistance of cancer cells to the drug while reducing the toxicity of the anticancer drug to cancer cells, and reducing the therapeutic effect of the drug. Therefore, in the present disclosure, by introducing the molecules for improving tumor microenvironment sensitivity through the monomer B, the tumor microenvironment sensitivity of the siRNA nanocapsule provided in the present disclosure is enhanced, thus a convenient condition is provided for triggered release of the siRNA nanocapsule at a lesion site, and the release efficiency of the siRNA is improved.

It should be noted that the specific selection of molecules for improving tumor microenvironment sensitivity is not limited in the present disclosure, for example, the molecules may be, but not limited to, molecules for improving temperature sensitivity, molecules for improving pH sensitivity, molecules for improving reduction sensitivity, molecules for improving enzyme sensitivity or molecules for improving physical signal stimulation sensitivity.

In some preferred embodiments, the monomer B includes molecules for improving reduction sensitivity. Glutathione (GSH) can break disulfide bonds, thus achieving the purpose of drug release. Glutathione concentration in cancer tissues is four times higher than that in normal tissues. This difference provides a convenient condition for the triggered release of anticancer nanomedicine at the lesion site. Thus, when the siRNA nanocapsule provided in the present disclosure is applied for treating cancer, the monomer B preferably includes molecules containing a disulfide bond. When biscystamine acrylamide is selected as the monomer B, environmentally responsive drug release can be effectively achieved.

It should be noted that the biscystamine acrylamide has a molecular structure as shown in Formula II:

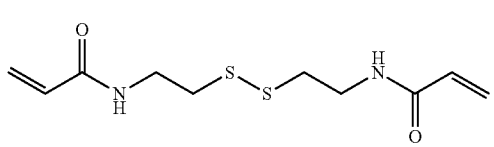

Formula II

In the present disclosure, the molecules for improving tumor microenvironment sensitivity may be directly linked to the targeting ligand, or may be linked to the targeting ligand through molecules for linking the targeting ligand. Preferably, the molecules for improving tumor microenvironment sensitivity are linked to the targeting ligand by the molecules for linking the targeting ligand. In some preferred embodiments, the molecules for linking the targeting ligand have one end linked to the molecules for improving tumor microenvironment sensitivity, and the other end linked to the targeting ligand. The targeting ligand, for example, may be, but not limited to acrylate polyethylene glycol succinyl carboxymethyl ester, acrylate polyethylene glycol maleimide or acrylate hyaluronic acid succinyl methyl ester. Preferably, the acrylate polyethylene glycol succinyl carboxymethyl ester is selected as a molecule for linking the targeting ligand, which has the advantages of improving the stability of the nanocapsule, prolonging the blood circulation time, facilitating modification of the targeting molecule and so on.

It should be noted that the acrylate polyethylene glycol succinyl carboxymethyl ester has a molecular structure as shown in Formula III:

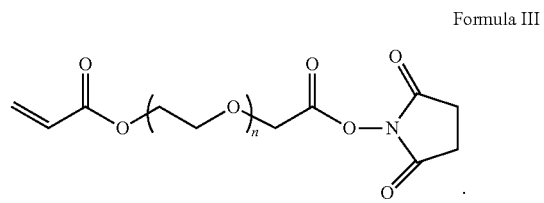

Formula III

Based on the novel self-encapsulation manner provided in the present disclosure, compared with existing delivery carriers, the siRNA nanocapsule provided in the present disclosure not only has a higher encapsulation rate, a smaller size, and stronger targeting ability, but also has good biocompatibility and biosafety, and thus has the potential to be widely used in clinics.

Specifically, when the monomer A is guanidyl acrylate, the monomer B is biscystamine acrylamide and acrylate polyethylene glycol succinyl carboxymethyl ester, and the targeting ligand is Angiopep-2, the siRNA molecules are encapsulated by a shell formed by cross-linking of disulfide bonds (SS), so as to protect the siRNA against degradation, intracellular siRNA can be triggered to be released in the cytoplasm in the case of a large amount of glutathione (GSH), and the specific LRP-1 ligand Angiopep-2 is coupled on the surface of the shell, so as to promote BBB penetration and targeting of GBM tumor tissues. Importantly, with this novel self-encapsulation strategy, small-sized siRNA nanocapsule and nearly 100% siRNA encapsulation are realized, resulting in high-efficient siRNA BBB penetration and GBM RNAi treatment. The brain delivery capacity and GBM RNAi effect of the siRNA nanocapsule provided in the present embodiment have been systematically assessed in vitro and in vivo, and the results indicate that it can effectively permeate BBB, be actively internalized by U87MG GBM cells, and can responsively release siRNA to cytoplasm, to realize specific gene knockout. In addition, the siRNA nanocapsule provided in the present embodiment further may achieve the effect of inducing strong anti-GBM by inhibiting the cancer suppressor genes, and prolong the survival time of orthotopic human GBM xenografted mice, with little toxic and side effects. These brain-targeted responsive siRNA nanocapsules have outstanding RNAi delivery capability, gene silencing and excellent biocompatibility, allowing them to exhibit relatively great potential for GBM treatment.

According to a second aspect of the present disclosure, the present disclosure further provides use of the above siRNA nanocapsule in preparation of a medicament for treating tumor.

Preferably, when specific monomer A, monomer B and targeting ligand are selected, such as guanidyl acrylate, biscystamine acrylamide, acrylate polyethylene glycol succinyl carboxymethyl ester and Angiopep-2, the siRNA nanocapsule provided in the present disclosure can be used for preparation of a medicament for treating glioblastoma, non-small cell lung cancer or cervical cancer, and has good inhibitory effects on cell lines such as U87MG, A549, Hela and X01.

According to a third aspect of the present disclosure, a method for preparing the above siRNA nanocapsule is further provided, including making the monomer A electrostatically bound with the siRNA and the monomer B to undergo polymerization reaction, to obtain a shell, and then linking a polymerization terminator with a targeting ligand on the shell to obtain the siRNA nanocapsule, wherein the monomer A includes molecules with a double bond at one end; and the monomer B includes molecules for improving tumor microenvironment sensitivity and molecules for linking the targeting ligand.

The preparation method provided in the present disclosure is simple in process and convenient in operation. Through the electrostatic binding effect between the monomer A and the siRNA, and the polymerization effect of the monomer B and the monomer A, the siRNA nanocapsule not only having a higher encapsulation rate, a smaller size, and stronger targeting ability, but also having good biocompatibility and biosafety can be prepared.

In some preferred embodiments, after mixing the siRNA with the monomer A, the monomer B is added, and radicals on the surface of siRNA undergo polymerization reaction under the action of an initiator and an optional catalyst, to form the shell encapsulating the siRNA.

When the initiator and the catalyst are simultaneously selected to participate in the polymerization reaction, the reaction rate is higher, and the time cost can be effectively saved.

Preferably, the initiator includes ammonium persulfate, preferably 0.05%-0.2% w/v ammonium persulfate solution, for example, the initiator may be, but not limited to, 0.05% w/v ammonium persulfate solution, 0.1% w/v ammonium persulfate solution, 0.15% w/v ammonium persulfate solution or 0.2% w/v ammonium persulfate solution, more preferably 0.1% w/v ammonium persulfate solution; preferably, the catalyst includes N,N,N',N'-tetramethylethylenediamine, preferably 0.2%-0.8% w/v N,N,N',N'-tetramethylethylenediamine solution, for example, the catalyst may be, but not limited to, 0.2% w/v N,N,N',N'-tetramethylethylenediamine solution, 0.3% w/v N,N,N',N'-tetramethylethylenediamine solution, 0.4% w/v N,N,N',N'-tetramethylethylenediamine solution, 0.5% w/v N,N,N',N'-tetramethylethylenediamine solution, 0.6% w/v N,N,N',N'-tetramethylethylenediamine solution, 0.7% w/v N,N,N',N'-tetramethylethylenediamine solution or 0.8% w/v N,N,N',N'-tetramethylethylenediamine solution, more preferably 0.5% w/v N,N,N',N'-tetramethylethylenediamine solution. Selecting a specific concentration of specific initiator and catalyst can further improve the reaction rate of the polymerization reaction.

Specifically, after mixing the siRNA with guanidyl acrylate, biscystamine acrylamide and acrylate polyethylene glycol succinyl carboxymethyl ester are added, and the radicals on the surface of siRNA undergo polymerization reaction under the action of ammonium persulfate and N,N,N',N'-tetramethylethylenediamine, to form the shell encapsulating the siRNA.

Preferably, the molar ratio of siRNA to guanidyl acrylate after mixing is 1:200-250, for example, the molar ratio may be, but not limited to 1:200, 1:210, 1:220, 1:230, 1:240 or 1:250, preferably 1:220; preferably, the molar ratio of guanidyl acrylate, biscystamine acrylamide to acrylate polyethylene glycol succinyl carboxymethyl ester is (3-8):(3-8):1, for example, the molar ratio may be, but not limited to 3:3:1, 8:8:1, 3:8:1, 8:3:1 or 5:5:1, preferably 5:5:1. By defining the amount ratio of respective raw materials, the utilization ratio of the raw materials can be made higher, and the reaction can be carried out more completely, thereby effectively saving the cost on the basis of ensuring the quality of the siRNA nanocapsule.

In some preferred embodiments, the siRNA is mixed with the guanidyl acrylate by means of stirring.

Preferably, the stirring includes at least one of the following conditions: the time is 10-20 minutes, for example, the time may be, but not limited to 10 minutes, 12 minutes, 15 minutes, 18 minutes or 20 minutes; the temperature is 20-25° C., for example, the temperature may be, but not limited to 20° C., 21° C., 22° C., 23° C., 24° C. or 25° C.; preferably, the stirring is carried out at the temperature of 20-25° C. for 15 minutes. By further optimizing the mixing condition of the siRNA and the guanidyl acrylate, the electrostatic binding of the siRNA and the guanidyl acrylate can be more sufficient, then the utilization rate of the raw materials is improved, and the cost is saved.

In some preferred embodiments, the polymerization reaction includes at least one of the following conditions: the polymerization reaction is carried out in an oxygen-free environment; the temperature is 0-5° C., for example, the temperature may be, but not limited to 0° C., 1° C., 2° C., 3° C., 4° C. or 5° C.; the time is 25-35 minutes, for example, the time may be, but not limited to 25 minutes, 28 minutes, 30 minutes, 32 minutes or 35 minutes; preferably, the polymerization reaction is carried out in an oxygen-free environment at a temperature of 0° C. for 30 minutes. In the above, the oxygen-free environment can be obtained by replacing a rare gas or nitrogen, preferably nitrogen is used, and thus the cost is lower. By adjusting and optimizing the condition of the polymerization reaction, the polymerization reaction can be made more sufficient, and the reaction efficiency can be improved.

In some preferred embodiments, after the shell is formed, the targeting ligand is added to carry out a linking reaction to obtain the siRNA nanocapsule; preferably, the targeting ligand includes Angiopep-2; and preferably, the molar ratio of the Angiopep-2 to acrylate polyethylene glycol succinyl carboxymethyl ester is 2-5:1, for example, the molar ratio may be, but not limited to, 2:1, 3:1, 4:1 or 5:1, preferably 3:1.

Preferably, the linking reaction includes at least one of the following conditions: the temperature is 20-25° C., for example, the temperature may be, but not limited to 20° C., 21° C., 22° C., 23° C., 24° C. or 25° C.; the time is 1.8-2.2 hours, for example, the time may be, but not limited to 1.8 hours, 1.9 hours, 2 hours, 2.1 hours or 2.2 hours; and preferably, the linking reaction is carried out at the temperature of 20-25° C. for 2 hours.

By optimizing and defining the usage amounts of the targeting ligand and the polymer for linking the targeting ligand, and the condition of the linking reaction, the linking reaction can be carried out more completely, effectively ensuring the targeting ability of the siRNA nanocapsule prepared.

In some specific embodiments, 10 µL of guanidyl acrylate is added to 500 µL of siRNA aqueous solution, and the resultant is stirred at 20-25° C. for 15 minutes to obtain a mixed liquid of siRNA and guanidyl acrylate in a molar ratio of 1:220; to the mixed liquid 20 μL of biscystamine acrylamide and 90 μL of acrylate polyethylene glycol succinyl carboxymethyl ester are added, to render a molar ratio of guanidyl acrylate, biscystamine acrylamide to acrylate polyethylene glycol succinyl carboxymethyl ester to be 5:5:1, then 20 μL of 0.1% ammonium persulfate solution and 10 μL of 0.5% N,N,N',N'-tetramethylethylenediamine solution are added. After polymerization reaction is carried out in an oxygen-free environment at 0° C. for 30 minutes, 45 μg of Angiopep-2 is added and linking reaction is carried out at 20-25° C. for 2 hours, to obtain the siRNA nanocapsule; a molar ratio of the Angiopep-2 to acrylate polyethylene glycol succinyl carboxymethyl ester is 3:1. Under the above specific reaction condition, the utilization ratio of respective raw materials is higher, the reaction is carried out more sufficiently, the prepared siRNA nanocapsule has a higher encapsulation rate and better targeting ability, and can effectively penetrate BBB and play a therapeutic effect on the GBM. The reaction process is shown in FIG. 1.

Preferably, after the linking reaction, a step of removing impurities is further included, and then the siRNA nanocapsule is obtained; preferably, the impurities are removed with a molecular weight cut-off of 10 kDa, and unreacted monomers are removed. Preferably, the impurities can be removed by a centrifugal filter with a molecular weight cut-off of 10 kDa. It is preferable to use PBS for ultrafiltration to exchange the raw reaction solution to PBS.

The present disclosure is further described below with specific examples, but it should be understood that these examples are merely for more detailed description, but should not be construed as limiting the present disclosure in any form.

Information of main reagents used in the examples of the present disclosure is as follows:

guanidyl acrylate was synthesized by citing the document ROS-Responsive Polymeric siRNA Nanomedicine Stabilized by Triple Interactions for the Robust Glioblastoma Combinational RNAi Therapy;

biscystamine acrylamide (sigma) acrylate polyethylene glycol succinyl carboxymethyl ester (JenKem);

Angiopep-2 (ChinaPeptides).

Example 1

The present example provides an siRNA nanocapsule, prepared by a following method:

10 μL of guanidyl acrylate was added to 500 μL of siRNA aqueous solution, and the resultant was stirred at 20-25° C. for 15 minutes to obtain a mixed liquid of siRNA and guanidyl acrylate in a molar ratio of 1:220; to the mixed liquid 20 μL of biscystamine acrylamide and 90 μL of acrylate polyethylene glycol succinyl carboxymethyl ester were added, to render a molar ratio of guanidyl acrylate, biscystamine acrylamide to acrylate polyethylene glycol succinyl carboxymethyl ester to be 5:5:1, then 20 μL of 0.1% ammonium persulfate solution and 10 μL of 0.5% N,N,N',N'-tetramethylethylenediamine solution were added. After polymerization reaction was carried out in an oxygen-free environment at 0° C. for 30 minutes, 45 μg of Angiopep-2 was added and linking reaction was carried out at 20-25° C. for 2 hours, to obtain the siRNA nanocapsule, wherein a molar ratio of the Angiopep-2 to acrylate polyethylene glycol succinyl carboxymethyl ester was 3:1.

Example 2

The present example provides an siRNA nanocapsule, prepared by a following method:

10 μL of guanidyl acrylate was added to 500 μL of siRNA aqueous solution, and the resultant was stirred at 20-25° C. for 10 minutes to obtain a mixed liquid of siRNA and guanidyl acrylate in a molar ratio of 1:220; to the mixed liquid 20 μL of biscystamine acrylamide and 90 μL of acrylate polyethylene glycol succinyl carboxymethyl ester were added, to render a molar ratio of guanidyl acrylate, biscystamine acrylamide to acrylate polyethylene glycol succinyl carboxymethyl ester to be 5:5:1, then 20 μL of 0.05% ammonium persulfate solution and 10 μL of 0.8% N,N,N',N'-tetramethylethylenediamine solution were added. After polymerization reaction was carried out in an oxygen-free environment at 5° C. for 25 minutes, 45 μg of Angiopep-2 was added and linking reaction was carried out at 20-25° C. for 2.2 hours, to obtain the siRNA nanocapsule; a molar ratio of the Angiopep-2 to acrylate polyethylene glycol succinyl carboxymethyl ester was 3:1.

Example 3

The present embodiment provides an siRNA nanocapsule, prepared by a following method:

10 μL of guanidyl acrylate was added to 500 μL of siRNA aqueous solution, and the resultant was stirred at 20-25° C. for 20 minutes to obtain a mixed liquid of siRNA and guanidyl acrylate in a molar ratio of 1:220; to the mixed liquid 20 μL of biscystamine acrylamide and 90 μL of acrylate polyethylene glycol succinyl carboxymethyl ester were added, to render a molar ratio of guanidyl acrylate, biscystamine acrylamide to acrylate polyethylene glycol succinyl carboxymethyl ester to be 5:5:1, then 20 μL of 0.2% ammonium persulfate solution and 10 μL of 0.2% N,N,N',N'-tetramethylethylenediamine solution were added. After polymerization reaction was carried out in an oxygen-free environment at 2° C. for 35 minutes, 45 μg of Angiopep-2 was added and linking reaction was carried out at 20-25° C. for 1.8 hours, to obtain the siRNA nanocapsule; a molar ratio of the Angiopep-2 to acrylate polyethylene glycol succinyl carboxymethyl ester was 3:1.

Example 4

The present example provides an siRNA nanocapsule, of which the preparation method is different from Example 1 merely in that the molar ratio of siRNA to guanidyl acrylate was 1:200.

Example 5

The present example provides an siRNA nanocapsule, of which the preparation method is different from Example 1 merely in that the molar ratio of siRNA to guanidyl acrylate was 1:250.

Example 6

The present example provides an siRNA nanocapsule, of which the preparation method is different from Example 1 merely in that the molar ratio of siRNA to guanidyl acrylate was 1:180.

Example 7

The present example provides an siRNA nanocapsule, of which the preparation method is different from Example 1 merely in that the molar ratio of guanidyl acrylate, biscystamine acrylamide to acrylate polyethylene glycol succinyl carboxymethyl ester was 3:3:1.

Example 8

The present example provides an siRNA nanocapsule, of which the preparation method is different from Example 1 merely in that the molar ratio of guanidyl acrylate, biscystamine acrylamide to acrylate polyethylene glycol succinyl carboxymethyl ester was 8:8:1.

Example 9

The present example provides an siRNA nanocapsule, of which the preparation method is different from Example 1 merely in that the molar ratio of guanidyl acrylate, biscystamine acrylamide to acrylate polyethylene glycol succinyl carboxymethyl ester was 2:10:1.

Example 10

The present example provides an siRNA nanocapsule, of which the preparation method is different from Example 1 merely in that the molar ratio of Angiopep-2 to acrylate polyethylene glycol succinyl carboxymethyl ester was 2:1.

Example 11

The present example provides an siRNA nanocapsule, of which the preparation method is different from Example 1 merely in that the molar ratio of Angiopep-2 to acrylate polyethylene glycol succinyl carboxymethyl ester was 5:1.

Example 12

The present example provides an siRNA nanocapsule, of which the preparation method is different from Example 1 merely in that the molar ratio of Angiopep-2 to acrylate polyethylene glycol succinyl carboxymethyl ester was 1:1.

Example 13

The present example provides an siRNA nanocapsule, of which the preparation method is different from Example 1 merely in that the guanidyl acrylate was substituted by spermine acrylate.

Example 14

The present example provides an siRNA nanocapsule, of which the preparation method is different from Example 1 merely in that the guanidyl acrylate was substituted by N-(3-aminopropyl)methacrylamide.

Example 15

The present example provides an siRNA nanocapsule, of which the preparation method is different from Example 1 merely in that acrylate polyethylene glycol succinyl carboxymethyl ester was substituted by acrylate polyethylene glycol maleimide.

Example 16

The present example provides an siRNA nanocapsule, of which the preparation method is different from Example 1 merely in that acrylate polyethylene glycol succinyl carboxymethyl ester was substituted by acrylate hyaluronic acid succinyl methyl ester.

Comparative Example 1

The present comparative example provides an siRNA nanocapsule, of which the preparation method is different from Example 1 merely in that the step of linking the targeting ligand was not included.

Comparative Example 2

The present comparative example provides an siRNA nanocapsule, of which the preparation method is different from Example 1 merely in that biscystamine acrylamide was substituted by 1,6-hexanediol dimethacrylate.

Comparative Example 3

Existing commercial transfection reagent Lipo2000.

In order to verify the effects of the siRNA nanocapsules provided in respective examples and comparative examples of the present disclosure, the following experimental examples were carried out.

Experimental Example 1 Cell Experiment (1) Flow cytometer and confocal microscope characterize endocytosis and intracellular release In the flow cytometer test, U87MG cells were inoculated in 6-well cell culture plates ($1 \times 10^6$ cells/well) and incubated at 37° C. for 24 hours, then 500 µL of PBS solution (200 nM Cy5-siRNA) of siRNA nanocapsule respectively provided in Examples 1-13 and Comparative Examples 1-3 was added to incubate for 4 hours, then the samples were absorbed away, and the cells were digested with 500 µL of pancreatin. The resulting cell suspension was centrifuged at 1000×g for 3 minutes, washed twice with PBS, re-dispersed in 500 µL of PBS, and underwent a flow cytometer (BD FACS Calibur, Becton Dickinson, USA) test within 1 hour, and 10000 cells were circled with Cell Quest software. In the competitive inhibition experiment, U87MG cells were first pre-treated with free Ang (200 µg/mL) for 4 h, then the siRNA nanocapsule provided in Example 1 was added.

The endocytosis and intracellular drug release behaviors were observed from CLSM photographs. After the U87MG cells were placed into 24-well cell culture plates containing microscope slides ($1 \times 10^5$ cells/well) and cultured for 24 hours, 50 µL of PBS solution (200 nM Cy5-siRNA) of siRNA nanocapsule respectively provided in Examples 1-13 and Comparative Examples 1-3 was added. After 4 hours of incubation, the culture medium was removed and washed twice with PBS. The lysosome was stained with lysosome red fluorescent probe (150 nmol/L) for 1 h, washed twice with PBS, fixed with 4% paraformaldehyde for 15 min, and washed twice with PBS. The nucleuses were stained with Hoechst 33342 for 15 minutes and then washed twice. Fluorescent pictures were taken by CLSM (TCS SP5).

The endocytosis and intracellular release of each group of siRNA nanocapsule in U87MG cells were verified by experiment, and results are shown in the following table:

| Group | Cellular Uptake | Intracellular Release | Group | Cellular Uptake | Intracellular Release |
| --- | --- | --- | --- | --- | --- |
| Example 1 | 170% | 155% | Example 11 | 65% | 58% |
| Example 2 | 165% | 143% | Example 12 | 58% | 43% |
| Example 3 | 168% | 149% | Example 13 | 55% | 41% |
| Example 4 | 142% | 122% | Example 14 | 74% | 59% |
| Example 5 | 128% | 102% | Example 15 | 62% | 40% |
| Example 6 | 52% | 47% | Example 16 | 70% | 52% |
| Example 7 | 90% | 76% | Comparative Example 1 | 47% | 36% |
| Example 8 | 92% | 67% | Comparative Example 2 | 28% | 20% |
| Example 9 | 85% | 50% | Comparative Example 3 | 108% | 92% |
| Example 10 | 63% | 49% | | | |

Figure 2:
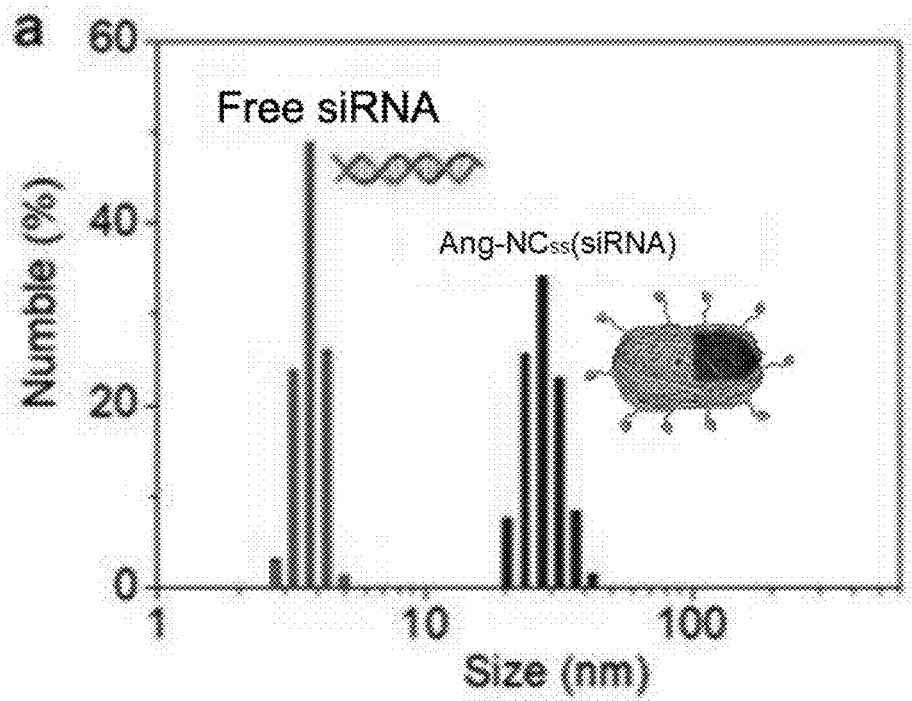
FIG. 2 is a graph of DLS test result of the siRNA nanocapsule provided in Example 1 of the present disclosure.

From the data in the table, it can be seen that the cellular uptake and intracellular release results of the siRNA nanocapsules provided in Examples 1-16 of the present disclosure are all superior to those of the comparative examples, indicating that the siRNA nanocapsule provided in the present disclosure has good capability of targeting and responsive release. In the above, the effects of Examples 1-5, 7-8 and 10-11 are all superior to those of Examples 6, 9, 12 and 13, indicating that the siRNA nanocapsule prepared according to the preparation conditions within the preferred range in the present disclosure has better capability of targeting and responsive release. The effect of Example 1 is the best, indicating that the capability of targeting and responsive release of the siRNA nanocapsule can be further improved by further adjusting and optimizing the condition parameters. It can be seen from the DLS test of the siRNA nanocapsule prepared in Example 1 that the nanoparticle size is uniform in distribution and has a size of 25.3 nm. The potential is 5.3 my, as shown in FIG. 2.

In order to save the experimental cost, all of the following experimental examples of the present disclosure were carried out by choosing Example 1 (Ang-NCss (siRNA)) having the best effect, Comparative Example 1 (NCss (siRNA)) without targeting ligand and Comparative Example 2 (Ang-NC (siRNA)) without introducing molecules for improving tumor microenvironment sensitivity.

Figure 3:
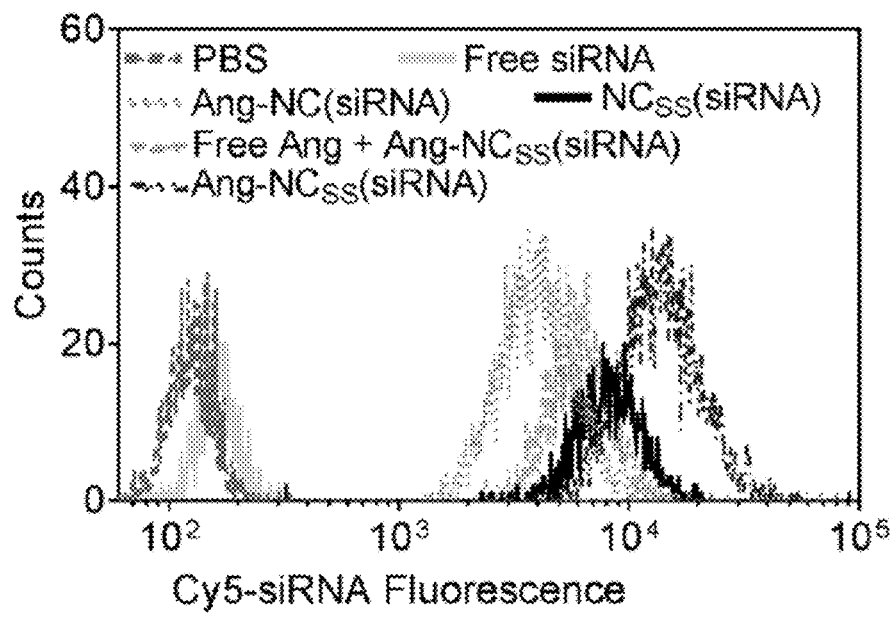
FIG. 3 is a graph of flow cytometry experiment result provided in Experimental Example 1 of the present disclosure.

Flow cytometry experiment (FIG. 3) indicates that the cellular uptake of Cy5-labeled Ang-NCss (siRNA) was the best in U87MG cells, which was 2.4 times and 1.9 times that of Ang-NC (siRNA) and NCss (siRNA), respectively. Moreover, pre-treating the U87MG cells with free Ang can significantly reduce cellular uptake of Ang-NCss (siRNA), thus confirming that these nanocapsules have an active targeting capability for U87MG cells.

Figure 4:
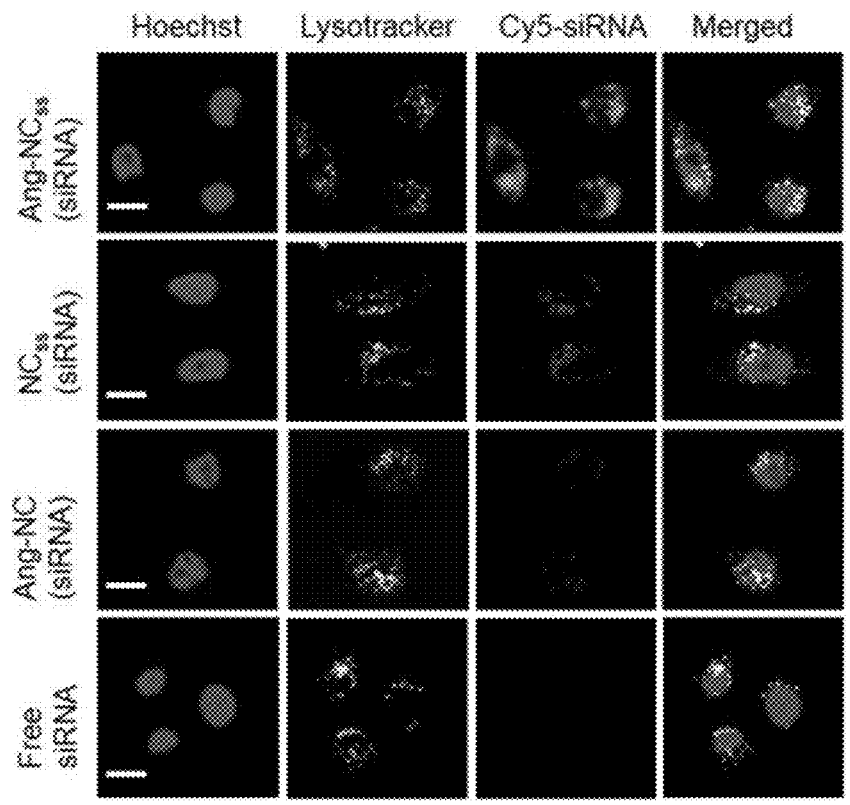
FIG. 4 is a graph of CLSM experiment result provided in Experimental Example 1 of the present disclosure.

CLSM (FIG. 4) results show that the U87MG cells incubated with Ang-NCss (siRNA) exhibited relatively strong cytoplasmic fluorescence, and can escape from endosomes in 4 h, which confirms effective cellular uptake and responsive intracellular siRNA release of the developed Ang-NCss (siRNA). The fluorescence of cells treated with non-targeting NCss (siRNA) and non-reducing Ang-NC (siRNA) was significantly less, and almost no fluorescence was detected in naked siRNA-incubated cells. This confirms that Ang-NCss (siRNA) can effectively target the U87MG cells by active endocytosis with the aid of Ang, and also can effectively release siRNA loading into the cytoplasm in an intracellular environment.

(2) In Vitro Cytotoxicity Assay

For the cytotoxicity test, U87MG cells were inoculated in 96-well plates ($5\times10^3$ cells/well) and incubated in DMEM containing 10% FBS (100 μL) for 24 hours. Thereafter, the culture medium was replaced with fresh culture medium respectively containing Ang-NCss (siRNA), NCss (siRNA), Ang-NC (siRNA) (siRNA 200 nM, 400 nM), and the cells were further incubated for 48 hours. Then, 10 μL of 3-(4, 5-dimethylthiazol-2-yl)-2,5-diphenyltetrazolium bromide (MTT) solution (5 mg/mL) was added, and the sample was further incubated at 37° C. for 4 h. The culture medium was removed, and 150 μL of dimethyl sulfoxide (DMSO) was added, so as to dissolve MTT-formazan crystal formed by live cells. Absorption values were detected at 570 nm using an ELIASA. Relative cell viability was determined by comparing absorbance at 570 nm with cells treated with PBS. Each piece of experimental data was measured in four groups in parallel (n=4).

Figure 5:
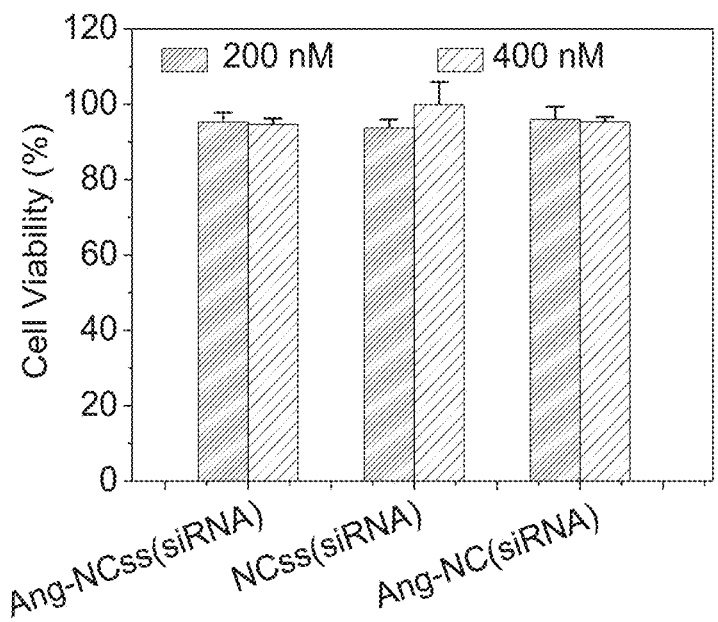
FIG. 5 is a graph of MTT experiment result provided in Experimental Example 1 of the present disclosure.

MTT (FIG. 5) analysis indicates that the siRNA nanocapsule at a concentration of 200 nM or 400 nM, including Ang-NCss (siRNA), NCss (siRNA) and Ang-NC (siRNA), was non-toxic to U87MG cells, indicating that they have good biocompatibility.

Experimental Example 2 Animal Experiment (1) Pharmacokinetic Study

200 μL of Ang-NCss (siRNA), NCss (siRNA), Ang-NC (siRNA) and naked siRNA (1 mg/kg Cy5-siRNA) were intravenously injected into nude mice by tail vein (n=3). At a prescribed time point after injection, ~50 μL of blood was taken from eye socket of the nude mouse. The blood sample drawn was immediately dissolved in 0.1 mL of lysis buffer (1% Triton X-100), added to 0.5 mL of DMSO and incubated overnight at R.T, then centrifuged (15 k rpm, 30 minutes) to extract Cy5-siRNA. The content of Cy5-siRNA in the supernatant was determined by fluorimetry. The half-life period of two stages (t½, α and t½, β) was calculated by fitting the experimental data using a Software Origin 8 exponential decay 2 model.

Figure 6:
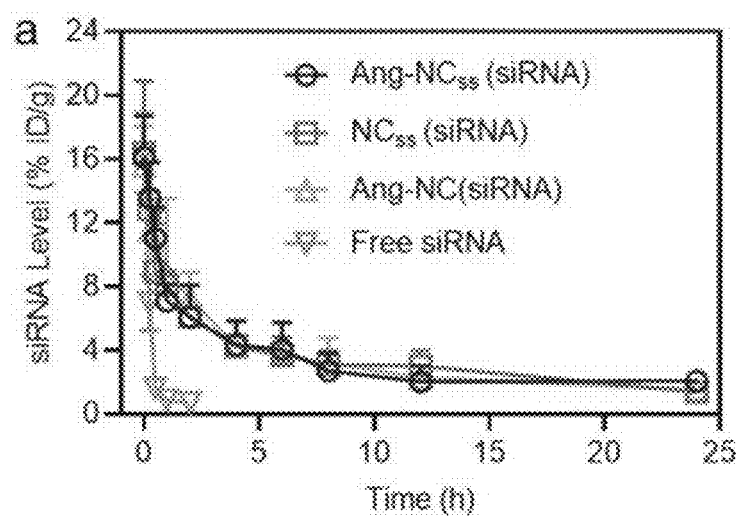
FIG. 6 is a graph of pharmacokinetic experiment result provided in Experimental Example 2 of the present disclosure.

Pharmacokinetic (FIG. 6) results indicate that Ang-NCss (siRNA) half-life period (t½, β) is 46 minutes, similar to NCss (siRNA) and Ang-NC (siRNA). In comparison, naked siRNA is quickly eliminated and the half-life period is as short as 5 minutes. These results demonstrate that the nanoparticles have relatively good biocompatibility.

(2) BBB Spanning Effect and Targeting Ability

Tumor-bearing mice were randomly grouped, and injected with 200 μL of Ang-NCss (siRNA), NCss (siRNA), Ang-NC (siRNA) and naked siRNA (1 mg/kg Cy5-siRNA) by tail vein. After the intravenous injection, the mice were scanned using a near-infrared fluorescence imaging system (Lumina, IVIS III) at predetermined time points (0, 1, 2, 4, 8, 12 and 24 hours) and the fluorescence images were analyzed.

Figure 7:
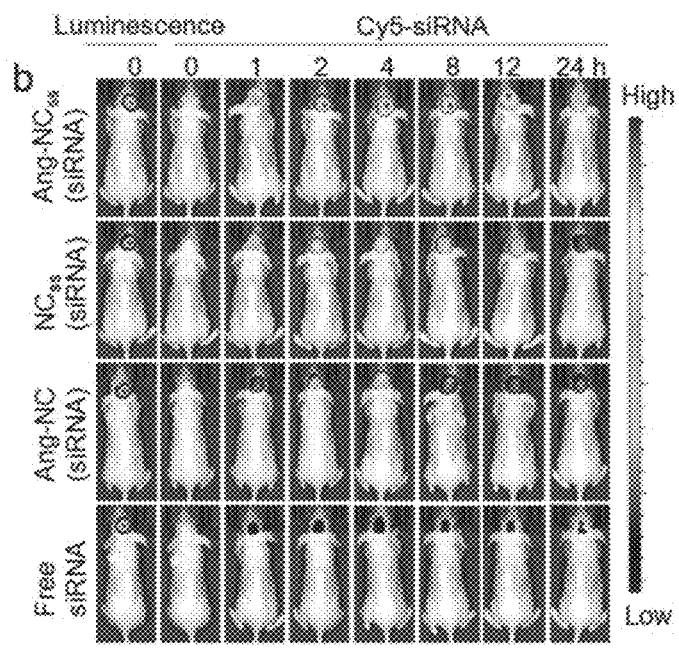
FIG. 7 is a graph of in vivo imaging result provided in Experimental Example 2 of the present disclosure.

In vivo imaging results (FIG. 7) show that strong Cy5 fluorescence was observed in the Ang-NCss (siRNA) group and sustained for 24 h, while relatively weak fluorescence was observed in mice of the control groups of NCss (siRNA), Ang-NC (siRNA) and naked siRNA, indicating that the nanoparticles have quite good capability to target tumors.

(3) Biodistribution

Tumor-bearing mice were randomly grouped, and intravenously injected with Ang-NCss (siRNA), NCss (siRNA), Ang-NC (siRNA) and naked siRNA (1 mg/kg Cy5-siRNA) by tail vein. Four hours after injection, the tumor-bearing mice were sacrificed. Major organs such as heart, liver, spleen, lung, kidney and brain were collected, washed, dried and weighed. Fluorescence images were acquired with a Lumina IVIS III near-infrared fluorescence imaging system. To quantify the cumulative amount of Cy5-siRNA in major organs, 0.6 mL of 1% Triton X-100 was homogenized at 70 K Hz for 10 minutes. Then 0.9 mL of DMSO was added, followed by incubation overnight at R.T. After centrifugation (15 k rpm, 30 minutes), the Cy5-siRNA in the supernatant was measured by fluorescence method, and the cumulative amount (% ID/g) per gram of tissue was calculated according to the standard curve.

Figure 8A:
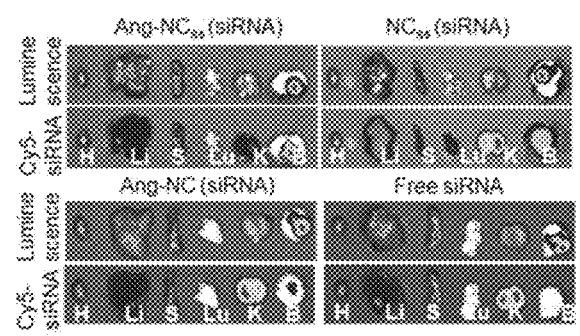
FIG. 8A is a graph of biodistribution result collected by a Lumina IVIS III near-infrared fluorescence imaging system provided in Experimental Example 2 of the present disclosure.
Figure 8B:
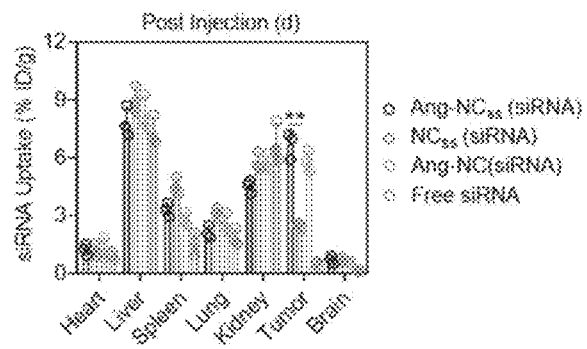
FIG. 8B is a bar graph of biodistribution result provided in Experimental Example 2 of the present disclosure.

Biodistribution (FIG. 8A and FIG. 8B) results show that the cumulative amount of Cy5-siRNA in tumors is 6.69% (% ID/g) in the Ang-NCss (siRNA) group, significantly higher than the free siRNA group, indicating that it has quite good ability to accumulate in tumor.

(4) Ang-NCss (siRNA) In Vivo Anti-Tumor Efficiency

Mice were randomly grouped and optically imaged using a bioluminescent Lumina IVIS III system. The tumor-bearing mice were weighed and randomly grouped into six groups (n=7): Ang-NCss (siPLK1), Ang-NCss (siCtrl), NCss (siPLK1), Ang-NC (siPLK1), naked siPLK1 and PBS. The mice were injected with siRNA by tail vein each 2 days at a dose of 2 mg/kg, the treatment was terminated at day 20, and one mouse was randomly chosen from each group to be subjected to experiments such as H&E and TUNEL, to analyze the health condition of each normal organ and the tumor tissue apoptosis condition of the mouse after treatment with the nanomedicine. In order to track U87MG-luc tumor proliferation condition, fluorescein (150 mg/kg) was injected intraperitoneally 10-15 minutes prior to imaging.

Figure 9:
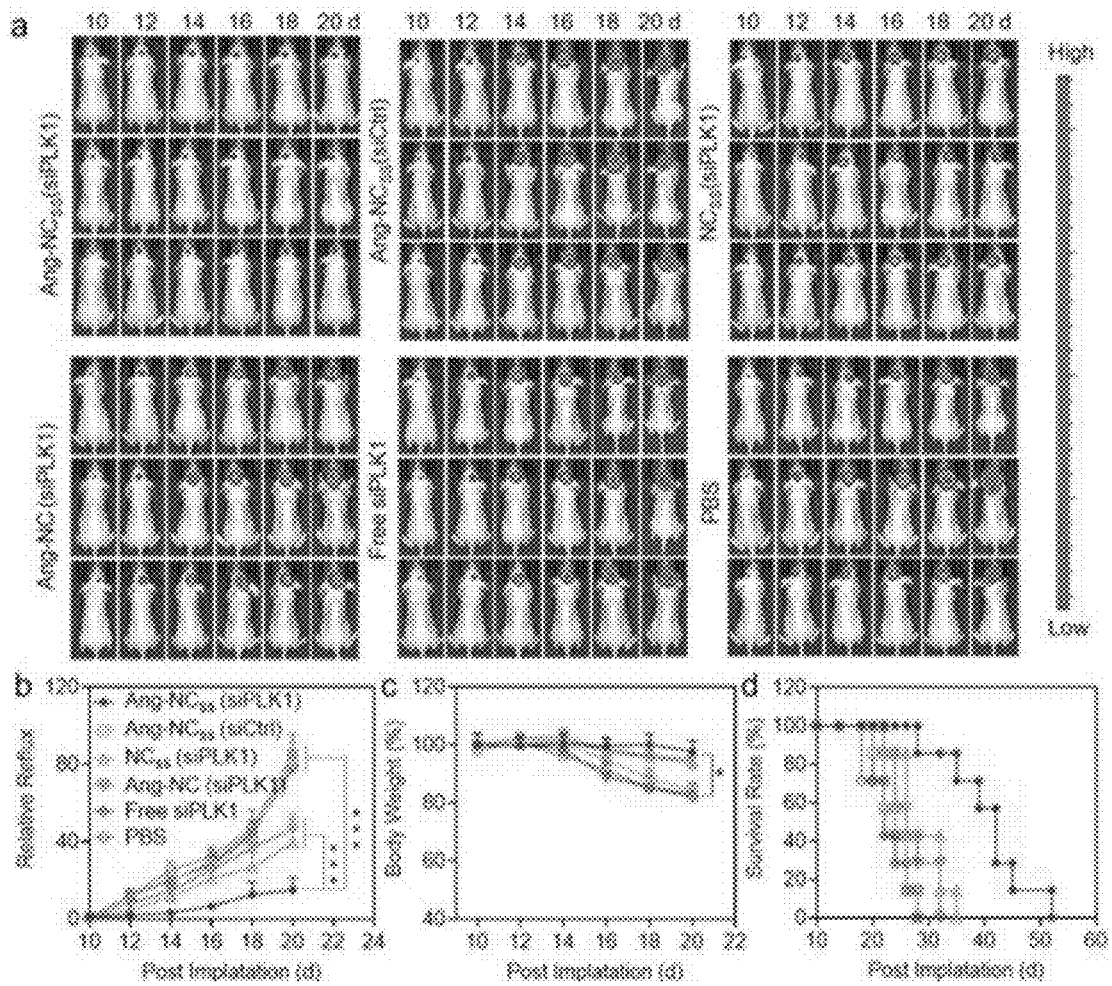
FIG. 9 is a graph of result of in vivo therapeutic effect on tumor-bearing mice provided in Experimental Example 2 of the present disclosure.
Figure 10:
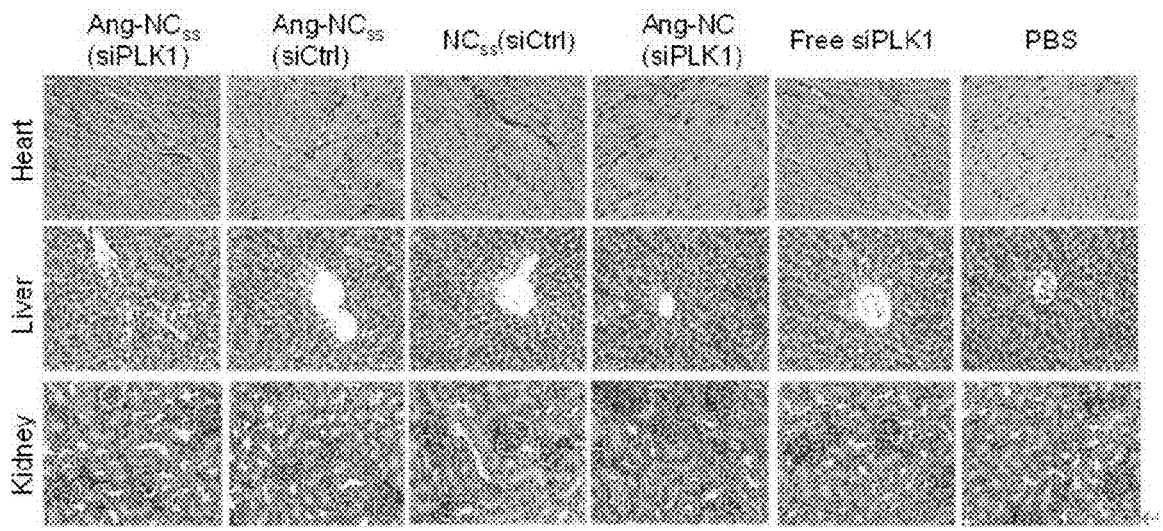
FIG. 10 is a graph of histological analysis result of H&E staining provided in Experimental Example 2 of the present disclosure.

Therapeutic experimental results of Ang-NCss (siRNA) in U87MG-luc-bearing BALB/c nude mice show that tumor growth can be significantly inhibited. The body weights in the Ang-NCss (siCtrl) group, free siPLK1 group and PBS group were significantly reduced within 20 days (about 30%). In comparison, the mice treated by Ang-NCss (siRNA) had slight change in body weight, indicating that the drug-loaded nanoparticle has little toxic and side effect. Ang-NCss (siPLK1) significantly prolongs the survival time of mice, with median survival time of up to 42 days, and the mice in Ang-NCss (siCtrl), free siPLK1 and PBS groups died within 28 days (the results are as shown in FIG. 9, in which a is biological fluorescence of U87MG-luc, b is relative photon quantity of different nanoparticles, c is weight change of the mice in the treatment process, and d is survival rate). Histological analysis result of H&E staining demonstrates that Ang-NCss (siPLK1) has little harm to major organs including heart, liver and kidney (FIG. 10). This result again indicates that Ang-NCss (siPLK1) has extremely low systemic toxicity.

Finally, it should be explained that the various examples above are merely used for illustrating the technical solutions of the present disclosure, rather than limiting the present disclosure; while the detailed description is made to the present disclosure with reference to the preceding examples, those ordinarily skilled in the art should understand that they still could modify the technical solutions recited in the preceding examples, or make equivalent substitutions to some or all of the technical features therein; these modifications or substitutions do not make the corresponding technical solutions essentially depart from the scope of the technical solutions of the various examples of the present disclosure.

What is claimed is:

1. An siRNA nanocapsule, comprising siRNA and a shell encapsulating the siRNA, wherein the siRNA is linked to the shell by electrostatic binding and, wherein the shell is obtained by polymerizing a monomer A and a monomer B, and a targeting ligand is further linked to outside of the shell, wherein
   the monomer A is guanidyl acrylate; and
   the monomer B comprises molecules for improving tumor microenvironment sensitivity, the molecules for improving tumor microenvironment sensitivity comprise biscystamine acrylamide.

2. A medicament for treating a tumor comprising the siRNA nanocapsule according to claim 1.

3. The siRNA nanocapsule according to claim 1, wherein the monomer B further comprises molecules for linking the targeting ligand, and the molecules for linking the targeting ligand comprise acrylate polyethylene glycol succinyl carboxymethyl ester, acrylate polyethylene glycol maleimide or acrylate hyaluronic acid succinyl methyl ester.

4. The siRNA nanocapsule according to claim 1, wherein the targeting ligand comprises Angiopep-2, RGD peptide, apolipoprotein E or transferrin.

* * * * *